(12) United States Patent
Buckel et al.

(10) Patent No.: US 10,028,998 B2
(45) Date of Patent: Jul. 24, 2018

(54) METHOD FOR TREATING AN INFLAMMATORY DISEASE AND/OR AN AUTOIMMUNE DISEASE WITH A SOLUBLE FCγRIIB

(71) Applicant: SppreMol GmbH, Martinsried / Munich (DE)

(72) Inventors: Peter Buckel, Bernried (DE); Peter Sondermann, Stockdorf (DE); Sascha Tillmanns, Munich (DE); Ingrid Berger, Munich (DE)

(73) Assignee: SUPPREMOL GMBH, Martinsried/Munich (DE)

( * ) Notice: Subject to any disclaimer, the term of this patent is extended or adjusted under 35 U.S.C. 154(b) by 0 days.

(21) Appl. No.: 13/663,527

(22) Filed: Oct. 30, 2012

(65) Prior Publication Data

US 2014/0120080 A1 May 1, 2014

(51) Int. Cl.
*A61K 38/00* (2006.01)
*A61K 38/17* (2006.01)
*C07K 14/735* (2006.01)
*A61K 38/13* (2006.01)

(52) U.S. Cl.
CPC .......... *A61K 38/1774* (2013.01); *A61K 38/13* (2013.01); *C07K 14/70535* (2013.01)

(58) Field of Classification Search
None
See application file for complete search history.

(56) References Cited

U.S. PATENT DOCUMENTS

| | | | |
|---|---|---|---|
| 6,849,719 B2 | 2/2005 | Shi et al. | |
| 7,504,482 B2 | 3/2009 | Sondermann et al. | |
| 8,853,363 B2 | 10/2014 | Huber et al. | |
| 2005/0002924 A1 | 1/2005 | Huber et al. | |
| 2015/0274804 A1 | 10/2015 | Sondermann et al. | |

FOREIGN PATENT DOCUMENTS

| | | |
|---|---|---|
| EP | 1870422 A1 | 12/2007 |
| WO | 00/32767 | 6/2000 |
| WO | 2003/043648 A2 | 5/2003 |
| WO | 2007/068047 | 12/2006 |
| WO | 2009/158696 | 6/2009 |
| WO | 2014/068012 A1 | 5/2014 |

OTHER PUBLICATIONS

Eu Clinical Trials Register, A Randomised, Multi-centre, Double-Blind, Placebo-Controlled, Single/Multiple Dose Escalation Phase Ib/IIa Clinical Trial to Investigate the Safety and Efficacy of Recombinant Human Soluble Fc-gamma Receptor IIb (SM101) for Intravenous Application in the Treatment of Patients with Chronic Adult Idiopathic Thr (Sep. 14, 2009).*

SuppreMol Press Release—SuppreMol releases positive interim Phase Ib/IIa results on SM101 in Primary Immune Thrombocytopenia (ITP) trials. Feb. 14, 2012.*
Clinical trial ISRCTN47912914, a phase Ib/IIa clinical trial to investigate the safety and efficacy of recombinant human soluble Fc-gamma receptor IIb (SM101) for intravenous application in the treatment of patients with chronic adult idiopathic thrombocytopenic purpura (ITP). ISRCTN Registry, last edited Apr. 19, 2011.*
SuppreMol Press Release, SuppreMol releases positive interim Phase Ib/IIa results on SM101 in Primary Immune Thrombocytopenia (ITP) trials. Feb. 14, 2012.*
SuppreMol Press Release: SuppreMol initiates Phase IIa clinical trial in Systemic Lupus Erythematosus (Sle) with its lead candidate SM101 (Jul. 11, 2011).*
Ahn et al., "Long-Term Danazol Therapy in Autoimmune Thrombocytopenia: Unmaintained Remission and Age-Dependent Response in Women", Annals of Internal Medicine, vol. 111, 1989, pp. 723-729.
Baccarani et al., "Splenectomy in Hematology. Current Practice and New Perspectives", Haematologica, vol. 84, 1999, pp. 431-436.
Berchtold et al., "Therapy of Chronic Idiopathic Thrombocytopenic Purpura in Adults", Blood, vol. 74, No. 7, Nov. 15, 1989, pp. 2309-2317.
Brighton et al., "Prospective Evaluation of the Clinical Usefulness of an Antigen-Specific Assay (MAIPA) in the Idiopathic Thrombocytopenic Purpura and Other Immune Thrombocytopenias", Blood, vol. 88, No. 1, Jul. 1, 1996, pp. 194-201.
British Society for Haematology , "Guidelines for the Investigation and Management of Idiopathic Thrombocytopenic Purpura in Adults, Children and in Pregnancy", British Journal of Haematology, vol. 120, 2003, pp. 574-596.
Burzynski , "New Options after First-Line Therapy for Chronic Immune Thrombocytopenic Purpura", American Journal of Health-System Pharmacy, vol. 66, 2009, pp. S11-S21.
Cines et al., "How I Treat: ITP", Blood, vol. 106, No. 7, 2005, pp. 2244-2251.
Feudjo-Tepie et al., "Prevalence of Diagnosed Chronic Immune Thrombocytopenic Purpura in the US: Analysis of a Large US Claim Database: A Rebuttal", Journal of Thrombosis and Haemostasis, vol. 6, 2008, pp. 711-712.

(Continued)

*Primary Examiner* — Dong Jiang
(74) *Attorney, Agent, or Firm* — K&L Gates LLP; Louis C. Cullman; Hal Gibson (57) ABSTRACT

The present invention relates to a method for treating or preventing either one or both of an inflammatory disease and an autoimmune disease in a patient, wherein the method comprises providing a pharmaceutical composition containing a therapeutically effective amount of soluble FcγR; administering said composition to a patient, followed by a safety period of several weeks, followed by a subsequent treatment cycle of at least two weekly administrations, wherein said therapeutically effective amount is effective to treat or prevent said disease in said patient. The present invention also provides a pharmaceutical composition in the form of a multiple-dosage-kit which contains sufficient amounts of administration doses of soluble FcγR for effectively treating or preventing inflammatory diseases and/or autoimmune diseases in a patient.

10 Claims, 1 Drawing Sheet

(56) References Cited

OTHER PUBLICATIONS

George et al., "Idiopathic Thrombocytopenic Pupura: A Practice Guideline Developed by Explicit Methods for the American Society of Hematology", Blood, vol. 88, No. 1, Jul. 1, 1996, pp. 3-40.

Godeau et al., "Dapsone for Chronic Autoimmune Thrombocytopenic Purpura: A Report of 66 Cases", British Journal of Haematology, vol. 97, 1997, pp. 336-339.

Godeau et al., "Treatment of Adult Chronic Autoimmune Thrombocytopenic Purpura with Repeated High-Dose Intravenous Immunoglobulin", Blood, vol. 82, No. 5, Sep. 1, 1993, pp. 1415-1421.

Provan et al., "Efficacy of Mycophenolate Mofetil as Single-Agent Therapy for Refractory Immune Thrombocytopenic Purpura", American Journal of Hematology, vol. 81, No. 1, 2006, pp. 19-25.

Rodeghiero et al., "Standardization of Terminology, Definitions and Outcome Criteria in Immune Thrombocytopenic Purpura of Adults and Children: Report of an International Working Group", Blood, vol. 113, No. 11, 2009, pp. 2386-2393.

Scaradavou et al., "Intravenous Anti-D Treatment of Immune Thrombocytopenic Purpura: Experience in 272 Patients", Blood, vol. 89, No. 8, Apr. 15, 1997, pp. 2689-2700.

Segal et al., "Prevalence of Immune Thrombocytopenia: Analyses of Administrative Data", Journal of Thrombosis and Haemostasis, vol. 4, 2006, pp. 2377-2383.

Suppremol, "Public Summary of Positive Opinion for Orphan Designation of Recombinant Soluble FC-Gamma Receptor IIb", EMEA/COMP/143892/2009, Jul. 29, 2008, 4 pages.

Ellsworth et al., 2009, "Recombinant Soluble Human FcγR1A (CD64A) Reduces Inflammation in Murine Collagen-Induced Arthritis", The Journal of Immunology, 182:7272-7279.

Ellsworth et al., 2008, "Targeting Immune Complex-Mediated Hypersensitivity with Recombinant Soluble Human FcγRIA (CD64A)", The Journal of Immunology, 280:580-589.

Magnusson et al., 2008, "Amelioration of collagen-induced arthritis by human recombinant soluble FCγRIIb", Clinical Immunology, 127:225-233.

International Search Report for International Application No. PCT/EP2013/072741 filed on Oct. 30, 2013.

Sondermann et al., Human FCγ receptor IIb expressed in *Escherichia coli* reveals IgG binding capability. Biological Chemistry, vol. 380, pp. 717-721 (1999).

SuppreMol Press Release, SuppreMol initiates phase Ib/IIa clinical trial with its lead candidate SM101 (Apr. 12, 2010, Munich, Germany).

SuppreMol Press Release: SuppreMol Completes Successful Pre-IND meeting with FDA. (Munich, Germany, Jan. 24, 2011).

\* cited by examiner

METHOD FOR TREATING AN INFLAMMATORY DISEASE AND/OR AN AUTOIMMUNE DISEASE WITH A SOLUBLE FCγRIIB

FIELD OF THE INVENTION

The present invention relates to a method for treating or preventing either one or both of an inflammatory disease and an autoimmune disease in a patient. Said method comprises administering a pharmaceutical composition containing a therapeutically effective amount of a soluble Fcγ receptor (FcγR). Specific schedules and time points of administration allow a surprisingly effective treatment or prevention of a disease in the patient.

BACKGROUND

WO 00/32767 describes soluble Fc receptors (FcRs) which are composed of only the extracellular part of the receptor and are not glycosylated. Due to the absence of the transmembrane domain and of the signal peptide, these proteins are present in a soluble form and not bound to cells. Furthermore the FcRs described in WO 00/32767 can be produced recombinantly and have been suggested for the treatment of autoimmune diseases due to their ability to bind the Fc part of antibodies without interfering with other components of the immune system. WO 00/32767 additionally describes the crystal structure of certain FcRs and the possibility of finding substances that inhibit the interaction of IgG with FcRs with the aid of these crystal structures. The elucidation of the crystal structure enables finding such inhibitors by screening the databases using available computer programs.

The invention which was defined in WO 03/043648 further developed the findings of WO 00/32767 and provides treatment methods especially for diseases like multiple sclerosis (MS), systemic lupus erythematosus (SLE), and rheumatoid arthritis (RA) and also for diseases with an elevated level of natural killer cells. When said receptors were produced recombinantly in prokaryotes and therefore were unglycosylated the inventors of WO 03/043648 surprisingly found that although the unglycosylated proteins were expected to be poorly soluble, the receptors could be purified with high concentrations of FcγR in a soluble form.

WO 03/043648 and other publication documents, that FcRs play an important role in defense reactions of the immune system. When pathogens have entered the blood circulation they are bound by immunoglobulins, also known as antibodies. Since the immune response to a pathogen is poylclonal, a multitude of antibodies bind to a pathogen, leading to the formation of a so called immune-complex (IC). ICs are subsequently phagocytised by specialized effector cells (e.g. phagocytes or macrophages) of the immune system and thus removed from the circulation. The phagocytosis is mediated by the binding of the Fc-part of the antibodies, forming the IC together with the pathogen, to FcRs on the aforementioned effector cells. Other effector cells of the immune system, such as natural killer cells, eosinophils and mast cells also carry FcRs on their surface which upon binding of immune complexes release stored mediators such as growth factors or toxins that support the immune response.

The FcRs of these effector cells also function as signal-transucing molecules that specifically bind immunoglobulins of various isotypes during the humoral immune response. In addition FcRs expressed on natural killer cells play a fundamental role in the destruction of antibody-coated target cells ("antibody-dependent cell-mediated cytotoxicity", ADCC).

However, in addition to the positive effects of FcRs in the defense against pathogens, overshooting reactions caused by the presence of auto-antibodies in patients may also occur which result in an undesired stimulation of the immune system which manifests itself especially as inflammatory or autoimmune diseases. Such immune reactions directed against the body's own substances remain a major medical problem and although there are approaches for treating them, these approaches are not equally effective in every patient.

All members of the FcγR-family are integral membrane glycoproteins, possessing extracellular domains related to a C2-set of immunoglobulin-related domains, having a single membrane spanning domain and an intracytoplasmic domain of variable length. There are three known Fcγ receptor forms, designated FcγRI (CD64), FcγRII (CD32), and FcγRIII (CD16). This invention specifically focuses on FcγRII (CD32).

FcγRII proteins are 40 KDa integral membrane glycoproteins which bind only bind the complexed IgG. These receptors are the most widely expressed FcγRs, present on all hematopoietic cells, including monocytes, macrophages, B cells, NK cells, neutrophils, mast cells, and platelets. There are three human FcγRII genes (FcγRII-a, FcγRII-b, FcγRII-c), all of which bind IgG in aggregates or immune complexes.

Inflammation is a process by which the body's white blood cells react to infection by foreign substances, such as bacteria and viruses. It is usually characterized by pain, swelling, warmth and redness of the affected tissue. Effector substances known as cytokines and prostaglandins control this process, and are released in an ordered and self-limiting cascade into the blood or affected tissues. The release of such effector substances increases the blood flow to the area of injury or infection. Some of the effector substances cause a leak of fluid into the tissues, resulting in swelling. This protective process may stimulate nerves and cause pain. These changes, when occurring for a limited period in the relevant area, work to the benefit of the body.

In autoimmune diseases the patient's immune system has lost the ability to discriminate between body-own ("self") and foreign proteins. In consequence, antibodies are generated that recognize "self"-proteins and form immune complexes which continuously activate the immune system because the "self"-protein is permanently produced and recognized as foreign. This chronic condition can persist for years leading in the end to severe organ damage and possibly to the death of the patient. There are many different autoimmune disorders which affect the body in various ways. For example, the brain is affected in individuals with multiple sclerosis, the gut is affected in individuals having Crohn's disease, and the synovium, bone and cartilage of various joints are affected in individuals suffering from rheumatoid arthritis. As autoimmune disorders progress destruction of one or more types of body tissues, abnormal growth of an organ, or changes in organ function may result. The autoimmune disorder may affect a single organ or tissue type or may affect multiple organs and tissues. Organs and tissues commonly affected by autoimmune disorders include red blood cells, blood vessels, connective tissues, endocrine glands (e.g., the thyroid or pancreas), muscles, joints, and the skin.

Examples of inflammatory and/or autoimmune disorders include, but are not limited to, primary immune thrombocytopenia (ITP), systemic lupus erythematosus (SLE), rheumatoid arthritis (RA), autoimmune haemolytic anaemia (AIHA), diabetes, Pemphigus vulgaris, Hashimoto's thyroiditis, autoimmune inner ear disease myasthenia gravis, pernicious anemia, Addison's disease, dermatomyositis, Sjogren's syndrome, dermatomyositis, multiple sclerosis, Reiter's syndrome, Graves disease, autoimmune hepatitis, familial adenomatous polyposis and ulcerative colitis.

Primary Immune Thrombocytopenia (ITP) is an autoimmune disorder characterized by a low platelet count (thrombocytopenia) of unknown aetiology. The immune system of ITP patients produces antibodies directed against their own platelets. These auto-antibodies form immune-complexes with platelets, which are subsequently recognised by Fc-gamma receptors (FcγRs) expressed on immune cells. This interaction triggers a wide range of responses which includes up-take, processing, antigen presentation as well as initiation of cellular cytotoxicity and release of inflammatory and immune mediators. As a result the platelet count in the blood is decreased and patients start suffering from bruising and potentially fatal spontaneous bleedings (purpura). The reason why the body reacts against its own platelets is currently unknown.

Primary Immune Thrombocytopenia is defined by platelet counts<100,000 µL (Rodeghiero, F. et al. (2009)) and is characterized clinically by an increased tendency to bruise. Clinically, ITP often presents as spontaneous bleeding in individuals with platelet counts of less than 20,000 µL. Subjects with platelet counts<10,000 µL may present with severe cutaneous bleeding, gingival bleeding, epistaxis, haematuria or menorrhagia. Some bleeding risk is present in subjects with platelet counts between 30,000 µL and 50,000 µL depending on the coexisting factors for bleeding (Cines D., (2005)).

Primary Immune Thrombocytopenia affects between 1 and 4 in 10,000 persons in the European Union, which corresponds to 50,000-200,000 persons in total (SuppreMol, 2008)). Children account for about half of all cases. In the United States, the ITP prevalence is estimated between 1 and 2.4 per 10,000 corresponding to up to 72,300 patients in total (Segal, J., (2006)), (Feudjo-Tepie, M., et al., (2008)). Children developing ITP experience acute disease followed by complete spontaneous remission, in most cases. In contrast, more adults will develop chronic ITP; a disease characterized by persistent moderate to severe thrombocytopenia that puts them at risk for bleeding with trauma and can also result in spontaneous haemorrhage of variable severity.

Diagnosis of ITP in adults is based on confirmed thrombocytopenia together with exclusion of other causes for the thrombocytopenia based on physical examination, complete blood count and blood smear results (George, J. et al., (1996)). Assays for anti-platelet antibodies are not sufficiently sensitive or specific to justify their routine use in the diagnosis of ITP (Brighton T. et al., (1996)).

The American Society of Hematology and the British Society for Haematology recommend initial treatment consisting of a full course of steroids or intravenous immunoglobulin. The initial treatment in adults with severe ITP is prednisone, usually at a dose of 1 mg/kg/day for 2 to 4 weeks. Patients who do not adequately respond to first line treatment are candidates for splenectomy. Two thirds of subjects with ITP who undergo splenectomy will achieve a normal platelet count (British Journal of Haematology, 2003)). Although splenectomy is a routine surgical procedure, it is endowed with a 0.8% risk of surgical mortality and a complication rate of 12% (Baccarani, U. et al., (1999)). Overall, the use of splenectomy for ITP is declining.

Subjects who do not respond to the first and second line treatment are classified as having chronic refractory ITP and this happens for 11-35% of ITP subjects. The treatment options available are:

High dose steroids: Oral dexamethasone of short duration in cycles and parenteral methylprednisolone. The response to the latter is faster therefore this is indicated when the platelet count needs to be increased as a priority. This response is transitory and requires maintenance therapy in the form of oral steroids.

High doses of IVIG: A small number of studies have shown that IVIG is effective and raises platelet count faster than steroids in adults with ITP. The doses used varied but 1 mg/kg/day for 2 days was generally recommended (Godeau, B. et al., (2003). The response is usually transitory but the infusions of IVIG can be repeated.

Intravenous anti-D: In one study this therapy has been shown to elevate the platelet counts in 79-90% of adults and lasted up to 3 weeks in 50% of those who responded (Scaradavou, A. et al., (1997)). This treatment is only effective in Rh D-positive non-splenectomised patients.

Vinca alkaloids: Vincristine or vinblastine, given i.v., can cause an increase in platelet count lasting 1-3 weeks. 50% of splenectomised patients respond. This response is sustained in only a small proportion of subjects (Berchtold, P. et al., (1989)).

Danazol: When administered at 200 mg 2-4 times daily for more than 2 months it resulted in a 60% response rate. It can be continued for over a year with less toxicity than long-term steroids. Age, sex, and the status of the spleen influence the responses (Ahn, Y. et al., (1989)).

Immunosuppressive agents: Azathioprine and cyclophosphamide have been successfully used (up to 25% of patients showed sustained response) but are slow acting and need long-term administration. Cyclosporin A can be given alone or with prednisone but carries a substantial risk of serious adverse reactions.

Dapsone: Administered orally for several weeks at a dose of 75 to 100 mg, resulted in a remission in half of the treated subjects but it was less effective in subjects with severe ITP and in splenectomised subjects (Godeau, B. et al., (1997)).

Experimental agents which have been used with good effect include thrombopoietic agents as well as rituximab or mycophenolate mofetil.

Rituximab, romiplostim, and eltrombopag are potential agents that have demonstrated the ability to increase platelet counts in patients with chronic ITP. Quite recently, the thrombopoietin-receptor agonists romiplostim and eltrombopag have been approved by the FDA for the treatment of chronic ITP in splenectomised patients. Romiplostim is also approved in the EU.

Romiplostim, a subcutaneous injectable analog of thrombopoietin, and eltrombopag, an oral non-peptide molecule, are indicated in the US for the treatment of thrombocytopenia in patients with chronic ITP who have an insufficient response to corticosteroids, immunoglobulins, or splenectomy.

Response was seen in splenectomised and non-splenectomised patients, including those who had no sustained benefit from multiple other agents. Further investigations need to be performed to define the risks of long-term use of thrombopoietic stimulating agents and the benefit of these novel agents in comparison to other therapies that provide a durable response off therapy (Burzynski J., (2009)).

Mycophenolate mofetil is a new immunosuppressive agent used in ITP. One study has shown 39% of patients achieved a sustained response. This agent may be a useful component of a combination therapy in patients with refractory ITP (Provan D. et al., (2006)).

In subjects requiring emergency treatment for low platelet count associated with active bleeding, high doses of i.v. corticosteroids or IVIG are indicated and transfusion of random donor platelets may be appropriate.

In spite of these different approaches for treating an autoimmune disease, they still represent a major health impairment and therefore further treatment approaches are needed.

SUMMARY

The present invention relates to a method for treating or preventing either one or both of an inflammatory disease and an autoimmune disease in a patient, wherein the method comprises providing a pharmaceutical composition containing a therapeutically effective amount of soluble FcγR; administering said composition to a patient, followed by a safety period of several weeks, followed by a subsequent treatment cycle of at least two weekly administrations, wherein said therapeutically effective amount is effective to treat or prevent said disease in said patient. The present invention also provides a pharmaceutical composition in the form of a multiple-dosage-kit which contains sufficient amounts of administration doses of soluble FcγR for effectively treating or preventing inflammatory diseases and/or autoimmune diseases in a patient.

DESCRIPTION

Accordingly, the object of the present invention was to provide a treatment or prevention method for diseases like systemic lupus erythematosus (SLE), rheumatoid arthritis (RA), autoimmune haemolytic anaemia (AIHA) and preferably primary immune thrombocytopenia (ITP).

The object was solved by a method for treating and/or preventing either one or both of an inflammatory disease and an autoimmune disease in a patient according to the present invention comprising providing a pharmaceutical composition containing a therapeutically effective amount of soluble Fcγ receptor (FcγR) and administering said composition to a patient, followed by a safety period of several weeks, followed by a subsequent treatment cycle of at least two weekly administrations, wherein said therapeutically effective amount is effective to treat or prevent said disease in said patient.

According to the present method the response to the therapy surprisingly is characterized by an increase of the median platelet count in ITP patients which persist during the 3 months follow-up period at the end of the therapy. In case the platelet count does not increase sufficiently the administration may be repeated. As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders.

In a preferred embodiment the inflammatory disease which can be treated by the present method is Primary Immune Thrombocytopenia (ITP), Systemic Lupus Erythematosus (SLE), Rheumatoid Arthritis (RA), or Autoimmune Haemolytic Anaemia (AIHA).

As used herein, the term "treating" and analogous terms refer to a management and care of a patient and/or the combating of disease or disorder.

As used herein, the terms "prevent", "preventing" and "prevention" refer to the prevention of the recurrence or onset of one or more symptoms of a disorder in a subject resulting from the administration of a prophylactic or therapeutic agent.

As used herein, a "therapeutically effective amount" refers to an amount of the therapeutic active component or agent which is sufficient to treat or ameliorate a disease or disorder, to delay the onset of a disease or provides any therapeutical benefit in the treatment or management of a disease.

The therapeutically effective amount per administration provided herein is from 0.3 to 5000 mg/kg, preferably from 0.3 to 1000 mg/kg, preferably from 1 to 250 mg/kg, preferably from 1 to 100 mg/kg, preferably at least 3 mg/kg, preferably from 3 to 50 mg/kg, preferably from 5 to 30 mg/kg, preferably from 10 to 30 mg/kg, preferably from 8 to 25 mg/kg, more preferably from 12 to 20 mg/kg, in particular 12 mg/kg.

Thus, it is preferred that a person of about 100 kg receives of about 1200 mg and a person of about 75 kg receives of about 900 mg of soluble FcγR, respectively.

As used herein, the term "soluble Fcγ receptor" and analogous terms refer to the extracellular part of the Fcγ receptor which can be dissolved in a liquid.

The pharmaceutical composition used in present invention contains at least one soluble Fcγ receptor in an amount, which is suitable to treat and/or prevent said disease in a patient. In one embodiment, the soluble FcγR is derived from FcγRIIb type receptor. In another embodiment, the soluble FcγR is SM101. SM101 is a recombinant, soluble, non-glycosylated version of the FcγRIIb as described WO 00/32767 and WO 03/043648, respectively.

The Fcγreceptor of the present invention comprises at least one of the amino acid sequences as shown in SEQ ID NO:1 (amino acid sequence of SM101) or SEQ ID NO:3 (amino acid sequence of FcγRIIb). In one preferred embodiment no mutations are introduced into the constructs when extending the N-termini and/or C-termini of the stated sequences in order to prevent antigenicity. However, it is theoretically possible to also introduce mutations or deletions into the extended sequences provided that they do not result in an undesired antigenicity.

Moreover, the soluble FcγR is of human origin. It is further characterized by the absence of transmembrane domains and signal peptide, which is described in e.g. WO 00/32767 (A1).

As used herein, the term "soluble FcγR is of human origin" and analogous terms refer to the extracellular part of the Fcγ receptor which can be dissolved in a liquid and which is derived from human and not from other species.

The soluble FcγR of the present invention in encoded by at least one of a nucleic acid sequence according to SEQ ID NO:2 (nucleic acid sequence coding SM101) or SEQ ID NO:4 (nucleic acid sequence coding FcγRIIb). These sequences can be cloned in an expression vector to produce the corresponding soluble FcγR by recombinant expression.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

In one embodiment the FcγRs can be expressed in prokaryotes and subsequently purified and refolded according to the description of WO 00/32767. The receptors have the advantage that they can be highly concentrated and hence only small volumes are necessary to administer adequately effective amounts. Furthermore, the costs of the pharmaceutical compositions according to the invention are very low since their production by recombinant expression in for example prokaryotes is simple and results in highly-purified and highly-concentrated protein preparations. Said soluble FcγR is therefore recombinant, soluble and non-glycosylated FcγR.

In another embodiment FcγRs can be easily and unexpensively produced in high purity in eukaryotic expression systems. Useful systems include eukaryotes with a specialized apparatus for the production of extracellular proteins, e.g. B cells. Other possible eukaryotic expression systems include, but are not limited to, CHO or HEK cells. Said soluble FcγR is therefore recombinant, soluble and glycosylated FcγR.

According to the present invention the pharmaceutical composition is administered at least once, in particular once on day 1, followed by a safety period of several weeks.

The term "several" refers to at least 2 weeks, preferably 3 weeks, more preferably 4 weeks, most preferably 5 weeks. The term "several weeks" refers to at least 14 days, preferably 21 days, more preferably 28 days, most preferably 35 days.

The safety period is at least 1 week, preferably 2 to 8 weeks, more preferably 4 to 6 weeks and most preferably 5 weeks.

The term "weekly" refers to a time period of about 4 to about 10 days, preferably 5 to 9 days, more preferably 6 to 8 days, most preferably 7 days.

It is further preferred that the subsequent treatment cycle comprises 2 to 7 weekly administrations between days 30 and 60, more preferable the subsequent treatment cycle are 3 to 5 weekly administrations between days 35 and 60 and most preferable the subsequent treatment cycle are 4 weekly administrations between days 35 and 56.

In one embodiment 1 to 250 mg/kg are administered on day 1, followed by a 2 to 8 week safety period, followed by a subsequent treatment cycle of 2 to 7 weekly administrations between days 30 and 60.

In another embodiment 5 to 30 mg/kg are administered on day 1, followed by a 4 to 6 week safety period, followed by a subsequent treatment cycle of 3 to 5 weekly administrations between days 35 and 60.

In a preferred embodiment 12 to 20 mg/kg are administered on day 1, followed by a 5 week safety period, followed by a subsequent treatment cycle of 4 weekly administrations between days 35 and 56.

The pharmaceutical composition is preferably injected. This injection is administered using intravenous infusions, subcutaneously or intramuscular.

Further the pharmaceutical composition may comprise other pharmaceutically acceptable carriers and/or excipients.

The term "pharmaceutically acceptable" means generally recognised pharmacopoeia for use in animals, and more particularly in humans.

The term "carrier" refers to a diluent, adjuvant, or vehicle with which the pharmaceutical composition is administered. Such pharmaceutical carriers can be sterile liquids, such as water and oils. Water is a preferred carrier when the pharmaceutical composition is administered intravenously. Saline solutions and aqueous dextrose and glycerol solutions can also be employed as liquid carriers, particularly for injectable solutions.

Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Furthermore, the pharmaceutical composition may be administered in combination with one or more other therapeutic agent or antibody, such as steroids or intravenous immunoglobulin, in particular corticosteroids, glucocorticoid prodrugs, e.g. prednisone, IVIG, anti-D, vinca alkaloids, e.g. vincristine or vinblastine, danazol, immunosuppressive agents, e.g. azathioprine, cyclophosphamide or cyclosporin A, dapsone, thrombopoicetic agents, rituximab, mycophenolate mofetil, romiplostim, eltrombopag, mycophenolate mofetil.

As used herein, the term "in combination" refers to the use of more than one prophylactic and/or therapeutic agent. The use of the term "in combination" does not restrict the order in which prophylactic and/or therapeutic agents are administered to a patient.

The present invention provides kits that can be used for the above described methods. It is also well known by a person skilled in the art that the pharmaceutical composition can be in the form of a multiple-dosage-kit containing sufficient amounts of administration doses of soluble FcγR for effectively treating or preventing inflammatory diseases and/or autoimmune diseases in a patient. In one embodiment, the pharmaceutical pack or kit comprises one or more containers filled with the pharmaceutical composition of the invention. Furthermore, one or more additional prophylactic or therapeutic agents useful for the treatment of a disease can also be included in the pharmaceutical pack or kit.

The following example will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE

Background

Primary Immune Thromocytopenia (ITP) is an autoimmune disorder characterized by a low platelet count below $100 \times 10^9$/L and an exclusion of secondary causes such as bacterial infections or hematological malignancies. Fcγ-receptors are involved in the clearance of immune complexes, the antibody-dependent cellular cytotoxicity, the secretion of mediators and indirectly the regulation of B cell proliferation and differentiation. SM101 has been investigated successfully in autoimmune models, toxicology studies in patients with ITP and Systemic Lupus Erythematosus (SLE).

Objectives

The primary objective was to evaluate the safety and tolerability of SM101 at increasing dose levels in patients with chronic ITP. Secondary objectives included efficacy in terms of platelet count and pharmacokinetic (PK) evaluation of SM101.

Methods

The Ib part of the clinical trial was designed as a randomized, double-blind, placebo-controlled, multi-center dose escalation study in 36 ITP patients. Each dosing cohort consisted of 4 verum and 2 placebo subjects. Major inclusion criteria included a diagnosis of chronic ITP for at least 6 months and a platelet count of less than $30 \times 10^9$/L at baseline. Concomitant corticosteroids were allowed at constant dose during the study. Eligible patients were dosed on day 1 with a 5 week safety period, followed up by the intended treatment cycle of 4 weekly infusions between day 35 and 56 and a final follow-up of 3 months.

Results

Figure 1:
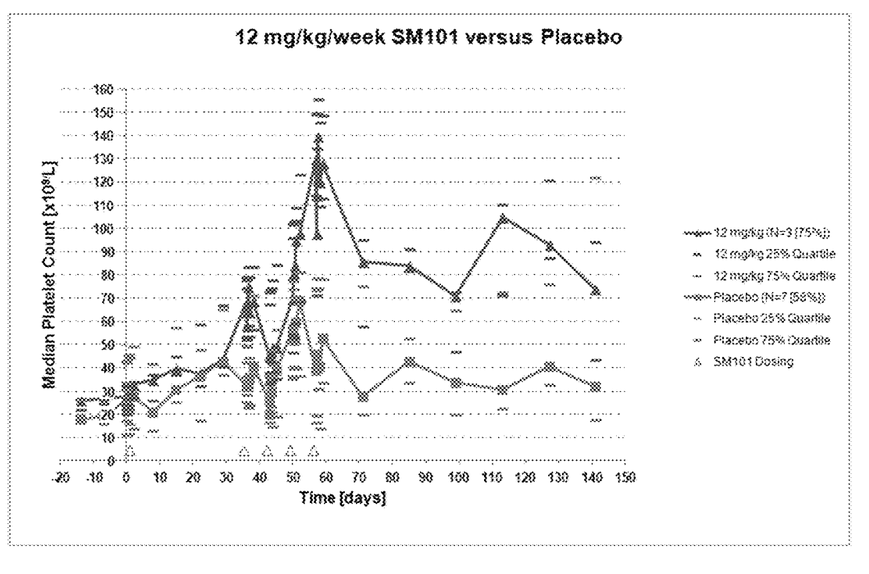
FIG. 1 shows the platelet response in Phase Ib with 12 mg/kg/week SM101 versus placebo.

In total, 36 ITP patients in 6 dose groups received 5 infusions of 0.3 to 12.0 mg/kg/week SM101 or placebo. 56% of the patients were females, 39% of the patients were splenectomized and 39% received concomitant corticosteroids prior to randomization. In the placebo group, 42% received rescue medication compared to 0 to 25% in the higher dose groups with SM101. SM101 plasma levels increased proportionally with dose and the mean t½ across all dose groups was 42.7 h with a range of 14.0 to 99.9 h. In terms of immunogenicity, no anti-drug-antibodies against SM101 were observed. For patients without ITP rescue therapy, the highest dose group with 12 mg/kg/week SM101 showed a sustained median platelet response over $50 \times 10^9$/L in comparison to placebo after one treatment cycle with 4 infusions (FIG. 1). This response persisted during the 3 months follow-up period with a median platelet count of approximately $70 \times 10^9$/L at the end of the clinical trial. The platelet response in the 12/mg/kg/week group started approximately 20 days after the beginning of the treatment cycle.

CONCLUSIONS

To the inventors knowledge, this is the first time that a soluble Fcγ receptor showed efficacy in a clinical trial. In the 12 mg/kg/week group, SM101 showed a clear platelet response in patients with ITP.

The duration of the platelet response persisted for at least 3 months after the last administration of SM101. Multiple doses of SM101 up to 12 mg/kg/week were well tolerated with no DLT or SAE.

All patents, publications and abstracts cited above are incorporated herein by reference in their entirety. Various embodiments of the invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the present invention as defined in the following claims.

REFERENCES

Rodeghiero F, S. R. et al., (2009) Standardization of terminology, definitions and outcome criteria in immune thrombocytopenic purpura of adults and children: report of an international working group. Blood, 113 (11), 2386-2393.

Cines D. B. and Bussel J. B, (2005) How I treat: ITP. Blood, 106 (7), 2244-2251

SuppreMol, Public Summary of Positive Opinion for Orphan Designation of recombinant human soluble FC-gamma receptor IIb, EMEA/COMP/143892/2008, 29 Jul. 2008

Segal, J. B. & Powe, N. R., (2006) Prevalence of immune thrombocytopenia: analyses of administrative data. Journal of Thrombosis and Haemostasis, 4, 2377-2383.

Feudjo-Tepie, M. A. et al., (2008) Prevalence of diagnosed chronic immune thrombocytopenic purpura in the US: analysis of a large US claim database: a rebuttal. Journal of Thrombosis and Haemostasis, 6, 711-712.

George, J. N. et al., (1996) Idiopathic Thrombocytopenic Pupura: A Practice Guideline Developed by Explicit Methods for the American Society of Hematology.

Brighton T. A. et al., (1996) Prospective evaluation of the clinical usefulness of an antigen-specific assay (MAIPA) in the idiopathic thrombocytopenic purpura and other immune thrombocytopenias. Blood, 88 (1), 194-201

British Society for Haematology; Guidelines for the Investigation and Management of Idiopathic thrombocytopenic purpura in adults, children and in pregnancy. British Journal of Haematology, 2003, 120, 574-596

Baccarani, U. et al., (1999) Splenectomy in hematology. Current practice and new perspectives. Haematologica, 84, 431-436.

Godeau, B. et al., (2003) Treatment of adult chronic autoimmune thrombocytopenic purpura with repeated high-dose intravenous immunoglobulin. Blood, 82, 1415-1421.

Scaradavou, A. et al., (1997) Intravenous anti-D treatment of immune thrombocytopenic purpura: experience in 272 patients. Blood, 89, 2689-2700.

Berchtold, P. & McMillan, R. (1989) Therapy of chronic idiopathic thrombocytopenic purpura in adults. Blood, 74, 2309-2317.

Ahn, Y. S. et al., (1989) Long-term danazol therapy in autoimmune thrombocytopenia: unmaintained remission and age-dependent response in women. Annals of Internal Medicine, 111, 723-729.

Godeau, B. et al., (1997) Dapsone for chronic autoimmune thrombocytopenic purpura: a report of 66 cases. British Journal of Haematology, 97, 336-339

Burzynski J., (2009) New options after first-line therapy for chronic immune thrombocytopenic purpura. *American Journal of Health-System Pharmacy*, 66, S11-S21

Provan D. et al., (2006) Efficacy of mycophenolate mofetil as single-agent therapy for refractory immune thrombocytopenic purpura. American Journal of Hematology, 81 (1), 19-25

The invention claimed is:

1. A method for treating either one or both of an inflammatory disease and an autoimmune disease in a patient, said method comprising:
providing a pharmaceutical composition containing a therapeutically effective amount of a soluble FcγRIIb;
administering said composition to the patient, followed by a safety period of two to eight weeks in which said composition is not administered to the patient, followed by a subsequent treatment cycle of at least two weekly administrations, wherein said therapeutically effective amount is effective to treat said disease in said patient;
wherein the therapeutically effective amount per administration is from 3 to 50 mg/kg, and wherein the disease is Primary Immune Thrombocytopenia (ITP), Systemic Lupus Erythematosus (SLE), Rheumatoid Arthritis (RA), or Autoimmune Haemolytic Anaemia (AIHA), and wherein the soluble FcγRIIb is SM101.

2. The method of claim 1, wherein the therapeutically effective amount per administration is from 8 to 25 mg/kg.

3. The method of claim 1, wherein the therapeutically effective amount per administration is 12 to 20 mg/kg.

4. The method of claim 1, wherein said administering is performed on day 1, followed by a 2 to 8 week safety period, followed by a subsequent treatment cycle of 2 to 7 weekly administrations.

5. The method of claim 1, wherein said administering is performed on day 1, followed by a 4 to 6 week safety period, followed by a subsequent treatment cycle of 3 to 5 weekly administrations.

6. The method of claim 1, wherein said administering is performed on day 1, followed by a 5 week safety period, followed by a subsequent treatment cycle of 4 weekly administrations between days 35 and 56.

7. The method of claim 1, wherein administration of the pharmaceutical composition is performed by injections or by infusions.

8. The method of claim 1, wherein the administration of the pharmaceutical composition is performed intravenously, subcutaneously or intramuscularly.

9. The method of claim 1, wherein the pharmaceutical composition comprises pharmaceutically acceptable carriers and/or excipients.

10. The method of claim 1, wherein the pharmaceutical composition is administered in combination with one or more other pharmaceutical agents and/or antibodies.

* * * * *

SEQUENCE LISTING

<160> NUMBER OF SEQ ID NOS: 4

<210> SEQ ID NO 1
<211> LENGTH: 177
<212> TYPE: PRT
<213> ORGANISM: Homo sapiens
<220> FEATURE:
<221> NAME/KEY: MISC_FEATURE
<222> LOCATION: (1)..(177)
<220> FEATURE:
<221> NAME/KEY: MISC_FEATURE
<222> LOCATION: (1)..(177)
<223> OTHER INFORMATION: SM101

<400> SEQUENCE: 1

```
Met Ala Pro Pro Lys Ala Val Leu Lys Leu Glu Pro Gln Trp Ile Asn
1               5                   10                  15

Val Leu Gln Glu Asp Ser Val Thr Leu Thr Cys Arg Gly Thr His Ser
            20                  25                  30

Pro Glu Ser Asp Ser Ile Gln Trp Phe His Asn Gly Asn Leu Ile Pro
        35                  40                  45

Thr His Thr Gln Pro Ser Tyr Arg Phe Lys Ala Asn Asn Asn Asp Ser
    50                  55                  60

Gly Glu Tyr Thr Cys Gln Thr Gly Gln Thr Ser Leu Ser Asp Pro Val
65                  70                  75                  80

His Leu Thr Val Leu Ser Glu Trp Leu Val Leu Gln Thr Pro His Leu
                85                  90                  95

Glu Phe Gln Glu Gly Glu Thr Ile Val Leu Arg Cys His Ser Trp Lys
            100                 105                 110

Asp Lys Pro Leu Val Lys Val Thr Phe Phe Gln Asn Gly Lys Ser Lys
        115                 120                 125

Lys Phe Ser Arg Ser Asp Pro Asn Phe Ser Ile Pro Gln Ala Asn His
    130                 135                 140

Ser His Ser Gly Asp Tyr His Cys Thr Gly Asn Ile Gly Tyr Thr Leu
145                 150                 155                 160

Tyr Ser Ser Lys Pro Val Thr Ile Thr Val Gln Ala Pro Ser Ser Ser
                165                 170                 175

Pro
```

<210> SEQ ID NO 2
<211> LENGTH: 534
<212> TYPE: DNA
<213> ORGANISM: Homo sapiens
<220> FEATURE:
<221> NAME/KEY: misc_feature
<222> LOCATION: (1)..(534)
<220> FEATURE:
<221> NAME/KEY: misc_feature
<222> LOCATION: (1)..(534)
<223> OTHER INFORMATION: SM101

<400> SEQUENCE: 2

```
atggcaccgc cgaaagcagt tctgaaactg gaaccgcagt ggattaacgt tctgcaggaa      60
gatagcgtta ccctgacctg tcgtggcacc catagcccgg aaagcgatag cattcagtgg     120
tttcacaacg gcaatctgat tccgacccat acccagccga gctatcgttt taaagcgaac     180
aacaacgata gcggcgaata tacctgtcag accggtcaga ccagcctgag cgatccggtt     240
catctgaccg ttctgagcga atggctggtt ctgcagaccc cgcatctgga atttcaggaa     300
ggcgaaacca ttgttctgcg ttgccacagc tggaaagata aaccgctggt taaagttacc     360
```

| | |
|---|---|
| ttcttccaga acggcaaaag caaaaaattc agccgtagcg atccgaattt tagcattccg | 420 |
| caggcgaatc atagccatag cggcgattat cattgtaccg gcaacattgg ctatacccctg | 480 |
| tatagcagca aaccggtgac cattaccgtt caggcgccga gcagcagccc gtaa | 534 |

<210> SEQ ID NO 3
<211> LENGTH: 181
<212> TYPE: PRT
<213> ORGANISM: Homo sapiens
<220> FEATURE:
<221> NAME/KEY: MISC_FEATURE
<222> LOCATION: (1)..(181)
<220> FEATURE:
<221> NAME/KEY: MISC_FEATURE
<222> LOCATION: (1)..(181)
<223> OTHER INFORMATION: FcgammaRIIb

<400> SEQUENCE: 3

```
Met Gly Thr Pro Ala Ala Pro Pro Lys Ala Val Leu Lys Leu Glu Pro
1               5                   10                  15

Gln Trp Ile Asn Val Leu Gln Glu Asp Ser Val Thr Leu Thr Cys Arg
            20                  25                  30

Gly Thr His Ser Pro Glu Ser Asp Ser Ile Gln Trp Phe His Asn Gly
        35                  40                  45

Asn Leu Ile Pro Thr His Thr Gln Pro Ser Tyr Arg Phe Lys Ala Asn
    50                  55                  60

Asn Asn Asp Ser Gly Glu Tyr Thr Cys Gln Thr Gly Gln Thr Ser Leu
65                  70                  75                  80

Ser Asp Pro Val His Leu Thr Val Leu Ser Glu Trp Leu Val Leu Gln
                85                  90                  95

Thr Pro His Leu Glu Phe Gln Glu Gly Glu Thr Ile Val Leu Arg Cys
            100                 105                 110

His Ser Trp Lys Asp Lys Pro Leu Val Lys Val Thr Phe Phe Gln Asn
        115                 120                 125

Gly Lys Ser Lys Lys Phe Ser Arg Ser Asp Pro Asn Phe Ser Ile Pro
    130                 135                 140

Gln Ala Asn His Ser His Ser Gly Asp Tyr His Cys Thr Gly Asn Ile
145                 150                 155                 160

Gly Tyr Thr Leu Tyr Ser Ser Lys Pro Val Thr Ile Thr Val Gln Ala
                165                 170                 175

Pro Ser Ser Ser Pro
            180
```

<210> SEQ ID NO 4
<211> LENGTH: 543
<212> TYPE: DNA
<213> ORGANISM: Homo sapiens
<220> FEATURE:
<221> NAME/KEY: misc_feature
<222> LOCATION: (1)..(543)
<220> FEATURE:
<221> NAME/KEY: misc_feature
<222> LOCATION: (1)..(543)
<223> OTHER INFORMATION: FcgammaRIIb

<400> SEQUENCE: 4

| | |
|---|---|
| atggggacac ctgcagctcc cccaaaggct gtgctgaaac tcgagcccca gtggatcaac | 60 |
| gtgctccagg aggactctgt gactctgaca tgccgggggga ctcacagccc tgagagcgac | 120 |
| tccattcagt ggttccacaa tgggaatctc attcccaccc acacgcagcc cagctacagg | 180 |
| ttcaaggcca acaacaatga cagcggggag tacacgtgcc agactggcca gaccagcctc | 240 |

```
agcgaccctg tgcatctgac tgtgctttct gagtggctgg tgctccagac ccctcacctg    300
gagttccagg agggagaaac catcgtgctg aggtgccaca gctggaagga caagcctctg    360
gtcaaggtca cattcttcca gaatggaaaa tccaagaaat tttcccgttc ggatcccaac    420
ttctccatcc cacaagcaaa ccacagtcac agtggtgatt accactgcac aggaaacata    480
ggctacacgc tgtactcatc caagcctgtg accatcactg tccaagctcc cagctcttca    540
ccg                                                                  543
```